(12) United States Patent
Rapp et al.

(10) Patent No.: US 8,071,026 B2
(45) Date of Patent: Dec. 6, 2011

(54) TISSUE PROCESSOR

(75) Inventors: Michael Rapp, Oftersheim (DE); Marc Konrad, Dossenheim (DE); Markus Dobusch, Wiesloch-Baiertal (DE); Stefan Kuenkel, Karlsruhe (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 187 days.

(21) Appl. No.: 12/545,430

(22) Filed: Aug. 21, 2009

(65) Prior Publication Data
US 2010/0055777 A1 Mar. 4, 2010

(30) Foreign Application Priority Data

Aug. 27, 2008 (DE) .................... 10 2008 039 861

(51) Int. Cl.
*G01N 21/00* (2006.01)
(52) U.S. Cl. ................ 422/65; 422/63; 422/64; 422/66; 422/67; 422/500; 422/501
(58) Field of Classification Search .............. 422/63–67, 422/500–501
See application file for complete search history.

(56) References Cited

U.S. PATENT DOCUMENTS

| 5,049,510 A | 9/1991 | Repasi et al. |
| 2002/0131896 A1* | 9/2002 | Hunnell et al. ................. 422/67 |
| 2007/0243626 A1 | 10/2007 | Windeyer et al. |

FOREIGN PATENT DOCUMENTS

| DE | 10 2005 057 191 | 6/2007 |
| DE | 10 2005 057 201 | 6/2007 |

* cited by examiner

*Primary Examiner* — Jyoti Nagpaul
(74) *Attorney, Agent, or Firm* — Schlee IP International, P.C.; Alexander R. Schlee

(57) ABSTRACT

A tissue processor is described that comprises a retort for processing histological samples using various reagents, a plurality of exchangeable reagent supply containers that each comprise at least one container opening, a system of conduits, a control device for conveying reagents out of the reagent supply containers through at least one reagent conduit into the retort, and system bottles. The reagent supply containers and the system bottles are connected via the pertinent reagent conduits to at least one valve. The valve is electrically connected to the control device such that at least one of filling and emptying of the system bottles with reagents from the reagent supply containers is controlled. This design allows differently dimensioned reagent supply containers while at the same time minimizing the space requirement for the reagent containers.

9 Claims, 3 Drawing Sheets

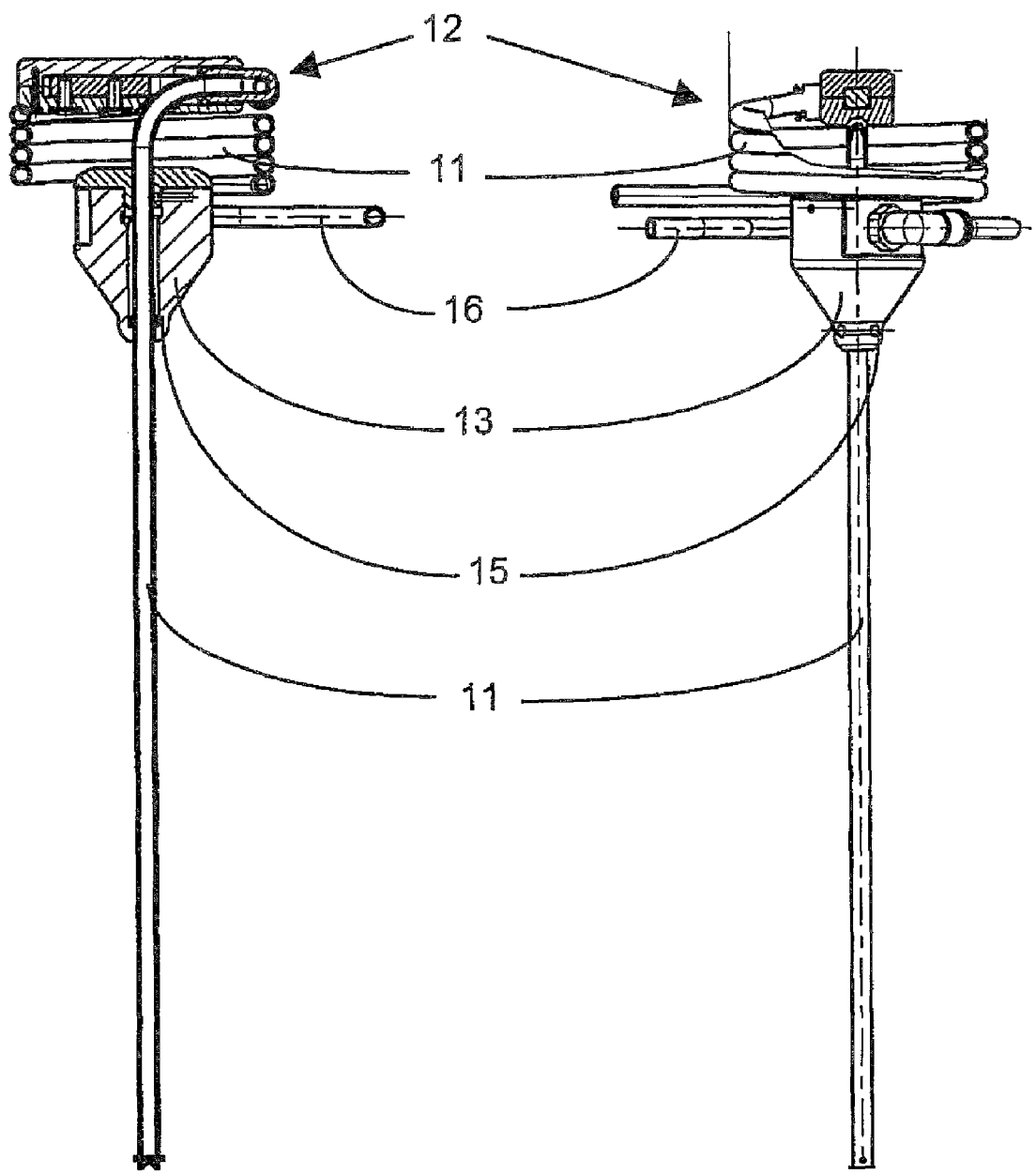

TISSUE PROCESSOR

CROSS-REFERENCE TO RELATED APPLICATION

This application claims the priority of the German patent application DE 102008039861.6 having a filing date of Aug. 27, 2008. The entire content of this prior German patent application DE 102008039861.6 is herewith incorporated by reference.

BACKGROUND OF THE INVENTION

The invention relates to a tissue processor having a retort for processing histological samples using different reagents, wherein said tissue processor comprises multiple exchangeable reagent supply containers that each comprise at least one container opening, and a system of conduits and a control device for conveying reagents out of the reagent supply containers through at least one reagent conduit into the retort.

Tissue processors are used for automatic processing of histological samples for subsequent preparation with a microtome, followed by microscopic investigation. The tissue of the sample must firstly, in multiple stages, be fixed, dewatered, cleaned, hardened, and then stabilized with paraffin. This is accomplished using various reagents to which the samples are exposed. The samples are also treated with identical reagents at different concentrations, so that a large number of process steps and a large number of reagent changes are necessary.

A tissue processor that permits largely automatic processing of samples is known from DE 10 2005 057 191 A1 and DE 10 2005 057 201 A1.

The tissue processor comprises a retort as a processing station for the sample. The retort is connected via a tubing system to multiple commercially usual reagent supply containers, having different dimensions, for the various reagents. The respective reagents can be pumped automatically, by way of a pump system and an electronic controller, from the supply containers into the retort and back again.

The reagent supply containers arranged in the tissue processor must from time to time be emptied and replaced with unexhausted reagents. A closure system having a conically shaped closure plug that is of internally hollow configuration is provided for this purpose in order to close off the container opening.

The reagent conduit is guided into the reagent supply container through the cavity in the closure plug. For adaptation to different overall reagent supply container heights, the closure system is equipped with a flexible bellows that comprises in the interior the reagent conduit and a connector, guided outward, for a gas conduit. The gas conduit serves for aeration and venting of the reagent supply containers during emptying and filling.

With the conically shaped closure plugs, reagent supply containers having different opening diameters can be connected with no need for additional adapters or other modifications to the tissue processor. Thanks to the conical configuration of the closure plug, differently dimensioned reagent supply containers can also be easily exchanged for others.

These directly exchangeable reagent supply containers have proven successful in practical use. It has been found, however, that the large dimensions and large number of reagents required create a large space requirement for the reagent supply containers.

SUMMARY OF THE INVENTION

It is therefore an object of the present invention to refine the tissue processor described initially, and in that context to continue to enable direct changing of commercially usual, differently dimensioned reagent supply containers but at the same time to minimize the space requirement for the reagent containers.

This object is achieved according to the present invention by arranging in addition to the reagent supply containers system bottles in the tissue processor and by connecting the reagent supply containers and the system bottles via the pertinent reagent conduits to at least one valve, the valve being electrically connected to the control device, and by controlling the filling and/or emptying of the system bottles with reagents from the reagent supply containers.

The invention is notable for the fact that in addition to the reagent supply containers, system bottles of smaller dimensions are arranged in the tissue processor, and the reagent supply containers and the system bottles are connected via the pertinent reagent conduits to a valve. By way of the valve, which is electrically connected to the control device, the system bottles can be directly filled from the reagent supply containers and/or directly emptied. Exhausted reagents from the system bottles can also be pumped back into the reagent supply containers. This is useful in particular when the reagent supply containers have been largely emptied and are now functioning as collection containers for exhausted reagents.

The result is that exhausted reagents in the system bottles can be replaced by unexhausted reagents in the larger reagent supply containers and/or regenerated, with no need to perform an exchange of the respective system bottles.

The retort can continue to be filled with reagents from the system bottles, or also with reagents from the reagent supply containers, and then emptied again.

The system bottles are notable for the fact that as compared with the reagent supply containers, they have a more compact configuration and dimensions adapted to the space available.

In a refinement of the invention, the valve is connected via the reagent conduit to the retort. Filling and/or emptying of the system bottles with reagents from the reagent supply containers is accomplished via the retort. The result of this is that not only unexhausted reagents but also, selectably, already-used reagents having a lower concentration, can be pumped out of the reagent supply containers into the system bottles. The result is that various system bottles can contain identical reagents at different concentrations.

In a further embodiment of the invention, there is provided for closing off the container opening a closure plug to which is connected, in addition to the reagent conduit, a gas conduit for aeration and venting of the reagent supply containers. The result is that air from the tissue processor, enriched with reagent vapors, cannot escape in uncontrolled fashion. Controlled aeration and venting of the retort is also thereby possible.

In a refinement of the invention, the gas conduit is connected to a pump. The system bottles and/or the reagent supply containers can thereby be filled or emptied by way of a change in pressure.

In a further embodiment of the invention, the retort is embodied in gas-tight fashion and is connected to the gas conduit. Filling and/or emptying of the system bottles and/or the reagent supply containers is thus accomplished by way of a direct change in pressure in the retort.

In a refinement of the invention, the reagent conduits and/or the gas conduit are embodied flexibly at the closure plug. The result is that reagent supply containers of different heights can be connected. The bellows used in the context of the tissue processors described initially can thus be omitted here.

In a refinement of the invention, the gas conduit is connected to a filter device. The filter device can also be provided outside the tissue processor. The result is that the reagent vapors, which is some cases are hazardous to health, cannot escape in uncontrolled fashion.

In a further embodiment of the invention, the gas conduit is connected to a condensate bottle for collecting condensed reagent vapor. This is necessary because the reagents in the retort are in some cases heated, and corresponding reagent vapors are thus produced and condense in the colder gas conduits outside the retort region. The reagent condensate is collected by way of a corresponding condensate separator and the condensate bottle that is connected.

In a refinement of the invention, the valve is embodied as a rotary valve to which the retort, the system bottles, and the reagent supply containers are connected, each via a separate reagent conduit. A very wide variety of connections can thereby be created.

BRIEF DESCRIPTION OF THE DRAWINGS

The invention will be further explained with reference to an exemplifying embodiment and with the aid of the schematic drawings, in which:

FIG. 3a is a sectioned depiction of the closure plug with reagent conduits and a gas conduit;
and
FIG. 3b is a view of the closure plug with reagent conduits and a gas conduit.

DETAILED DESCRIPTION OF THE DRAWINGS

Figure 1:
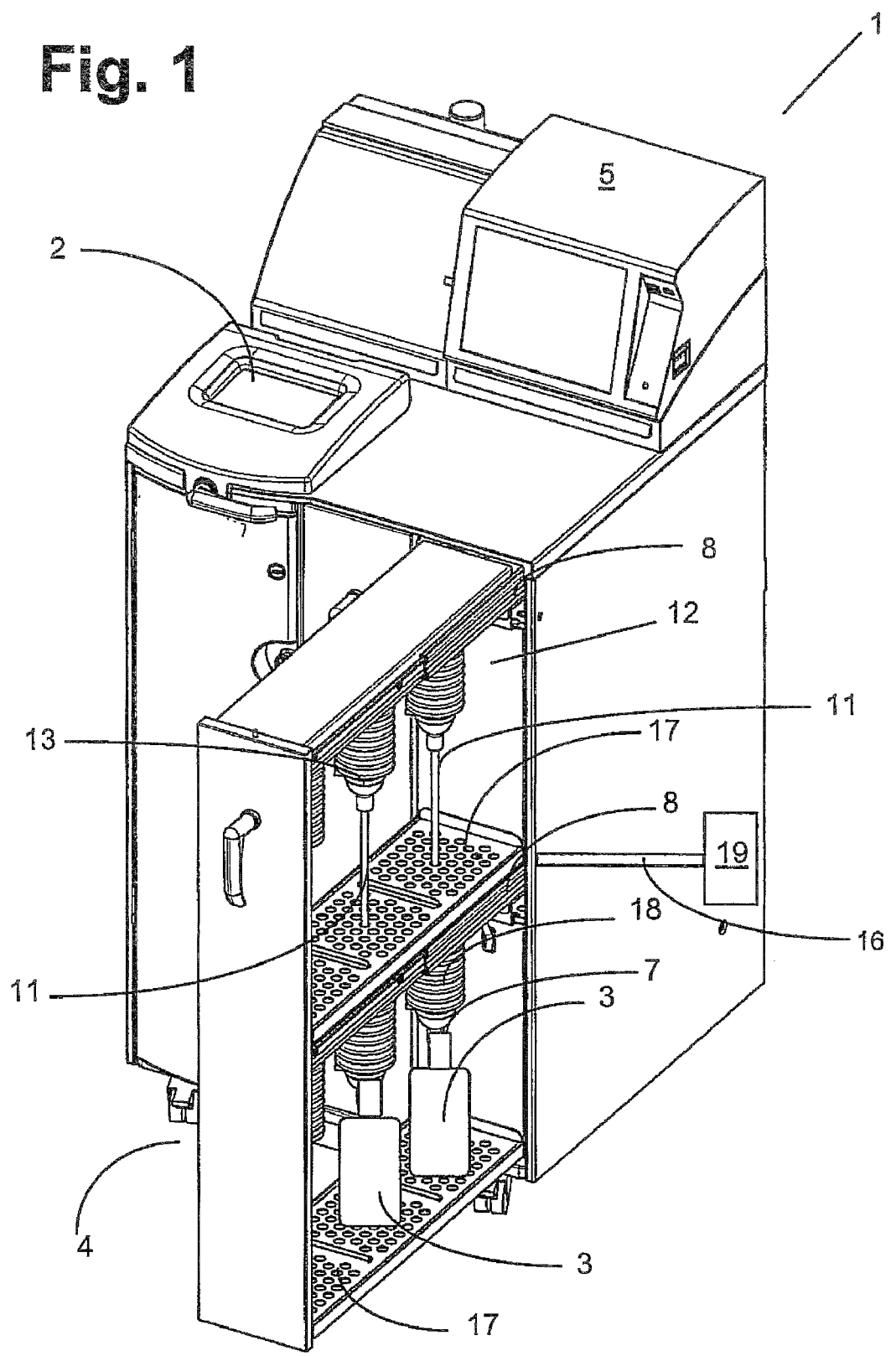
FIG. 1 is a view of the tissue processor with a drawer.

FIG. 1 is a view of a tissue processor 1 having a retort 2 for the processing of samples, and a control device 5. Tissue processor 1 is equipped with a drawer 4 that is connected via telescoping rails 8 to the housing of processor 1. Drawer 4 comprises two trays 17, arranged one above another, as supports for multiple reagent supply containers 3 and system bottles (not depicted). Reagent supply containers 3 are respectively connected via a closure system 12 to a system of conduits through which the reagents are conveyed out of reagent supply containers 3 into retort 2 and back again therefrom. Also provided is a gas conduit 16 that is connected to a filter device 19 in tissue processor 1 and that filters vapors emerging from reagent supply containers 3.

Closure system 12 comprises a conically shaped closure plug 13 having a reagent conduit 11, guided in the interior of closure plug 13, that projects through container opening 7 into the interior of reagent supply container 3. Closure plug 13 is movably mounted so that different overall heights of reagent supply containers 3 can be compensated for.

Figure 2:
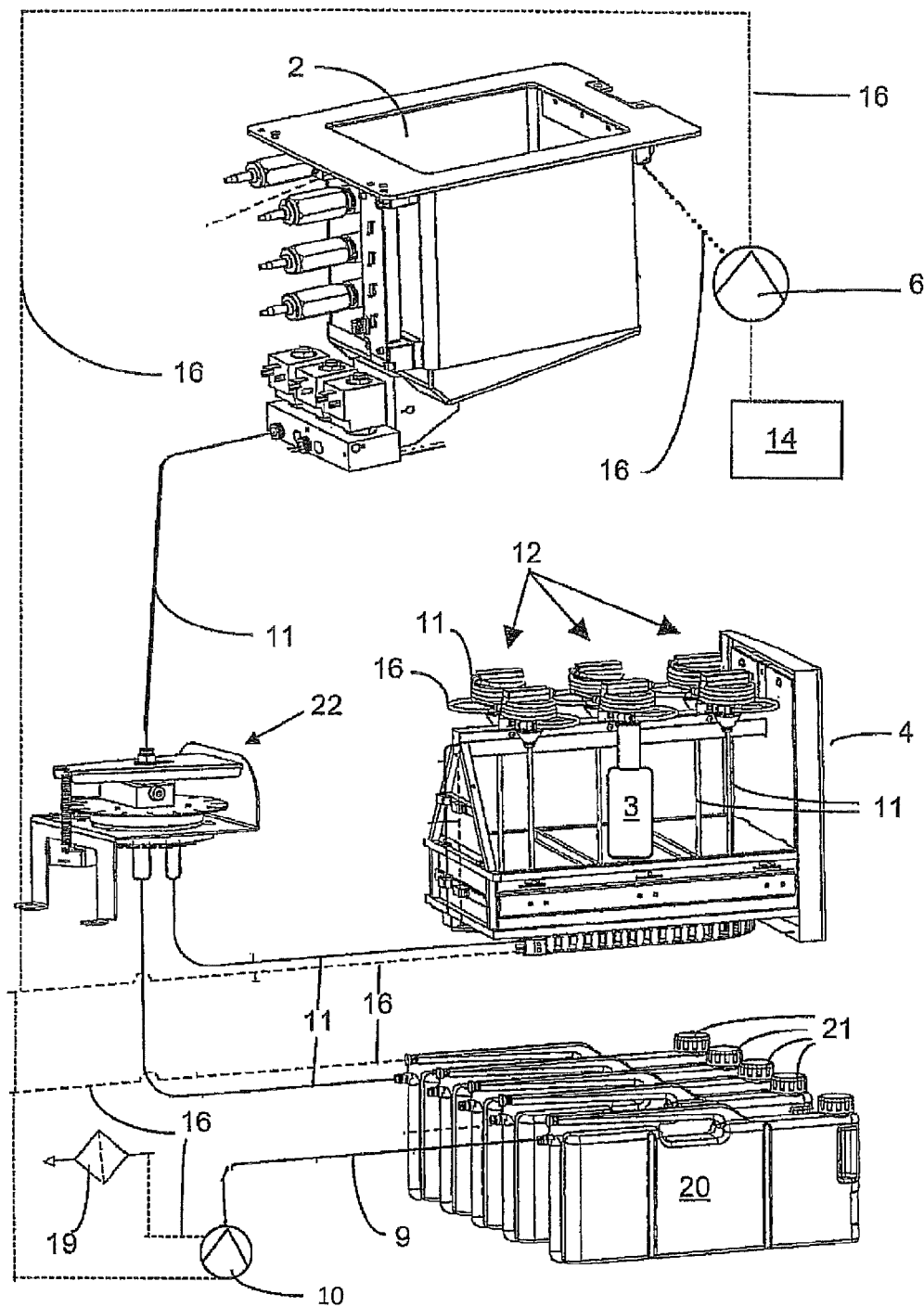
FIG. 2 depicts the reagent supply containers and the system bottles.

FIG. 2 is a detail view of reagent supply containers 3 and system bottles 21, and of the connections to a rotary valve 22 and to retort 2. Reagent supply containers 3 are arranged in drawer 4 and each connected to closure system 12. Each of the closure systems 12 is equipped with a separate reagent conduit 11 and a separate gas conduit 16. Reagent conduits 11 are connected to rotary valve 22.

System bottles 21 likewise comprise reagent conduits 11 and gas conduits 16. Reagent conduits 11 are connected to rotary valve 22 so that a connection between reagent supply container bottles 3 and system bottles 21 can be created via rotary valve 22. For reasons of clarity, only a single respective reagent conduit 16 from reagent supply containers 3 and system bottles 21 to rotary valve 22 is depicted here.

Gas conduits 16 of reagent supply containers 3 and gas conduits 16 from system bottles 21 are connected to a condensate separator 10 so that condensing vapors can be directed, in this case via a connected condensate conduit 9, into a condensate bottle 20. Associated with condensate separator 10 is an outgoing gas conduit 16 that is connected to filter device 19.

Rotary valve 22 is connected via reagent conduit 11 to retort 2, so that a connection can be created selectably between reagent supply containers 3 and system bottles 21, or reagent supply containers 3 and retort 2, or system bottles 21 and retort 2.

Retort 2 is embodied to be sealable in pressure-tight fashion, and is connected via gas conduit 16 to a pressure valve 6 and a pump 14. With pump 14, a change in pressure can be produced in retort 2 in order to pump the reagent liquid either into the retort or back out of the retort. The corresponding containers 3, 21 can be preselected by means of rotary valve 22.

The electrical connections between rotary valve 22, condensate separator 10, and pump 14 and control device 5 (FIG. 1) are not depicted for reasons of simplicity.

FIG. 3a is a sectioned depiction of closure system 12 with closure plug 13 and reagent conduit 11 guided into the interior, which conduit is arranged helically outside closure plug 13. Closure plug 13 is equipped with gas openings 15 that are connected to gas conduits 16. The reagent containers and system bottles can be aerated and vented through gas openings 15 and gas conduits 16.

FIG. 3b is a view of closure system 12 with the helically coiled reagent conduits 11 and with an angle piece 18 through which gas conduit 16 is connected to gas openings 15.

LIST OF COMPONENT PARTS

1 Tissue processor
2 Retort
3 Reagent supply container
4 Drawer
5 Control device
6 Pressure valve
7 Container opening
8 Telescoping rail
9 Condensate conduit
10 Condensate separator
11 Reagent conduit
12 Closure system
13 Closure plug
14 Pump
15 Annular opening
16 Gas conduit
17 Tray
18 Angle piece
19 Filter device
20 Condensate bottle
21 System bottle
22 Rotary valve

The invention claimed is:

1. A tissue processor comprising:
a retort for processing histological samples using various reagents;
a plurality of exchangeable reagent supply containers that each comprise at least one container opening;
a system of conduits;
a control device for conveying reagents out of the reagent supply containers through at least one reagent conduit into the retort; and system bottles; wherein the reagent supply containers and the system bottles are connected via the pertinent reagent conduits to at least one valve; and the valve is electrically connected to the control device; and conduits connect a plurality of the system bottles via the valve to at least one of the reagent supply containers, wherein each of the system bottles in the plurality of system bottles is filled with the same reagent, but distinguishes in concentration from one system bottle to another.

2. The tissue processor according to claim 1, wherein the valve is connected via the reagent conduit to the retort such that at least one of filling and emptying of the system bottles with reagents from the reagent supply containers is accomplished via the retort.

3. The tissue processor according to claim 2, wherein the retort is gas-tight and connected to the gas conduit, the tissue processor further comprising means for at least one of filling and emptying of the system bottles by way of a change in pressure in the retort.

4. The tissue processor according to claim 1, further comprising a closure plug for closing the container opening, said closure plug being connected to a reagent conduit and to a gas conduit for aeration and venting of the reagent supply containers.

5. The tissue processor according to claim 4, wherein the gas conduit is connected to a pump, and the tissue processor further comprises means for at least one of filling and emptying of the system bottles by way of a change in pressure.

6. The tissue processor according to claim 4, wherein at least one of the reagent conduit and the gas conduit is flexible at the closure plug.

7. The tissue processor according to claim 1, further comprising a filter device, wherein the gas conduit is connected to said filter device.

8. The tissue processor according to claim 1, further comprising a condensate bottle, wherein the gas conduit is connected to said condensate bottle for collecting condensed reagent vapor.

9. The tissue processor according to claim 1, wherein the valve is a rotary valve.

* * * * *